(12) United States Patent
Zuidema et al.

(10) Patent No.: US 7,776,081 B2
(45) Date of Patent: Aug. 17, 2010

(54) DEVICES AND METHODS FOR ANASTOMOSIS

(75) Inventors: Johan Zuidema, Groningen (NL); Jan Bart Hak, Groningen (NL); Jan Smit, Schagen (NL); Rutger Jan Ploeg, Haren (NL); Hendrik Othmar ten Cate Hoedemaker, Tynaarlo (NL)

(73) Assignee: Polyganics B.V., Groningen (NL)

( * ) Notice: Subject to any disclaimer, the term of this patent is extended or adjusted under 35 U.S.C. 154(b) by 518 days.

(21) Appl. No.: 11/581,793

(22) Filed: Oct. 16, 2006

(65) Prior Publication Data

US 2007/0118157 A1    May 24, 2007

Related U.S. Application Data

(63) Continuation of application No. PCT/NL2005/000290, filed on Apr. 20, 2005.

(30) Foreign Application Priority Data

Apr. 20, 2004    (EP)    ................................ 04076251

(51) Int. Cl.
*A61F 2/06* (2006.01)
(52) U.S. Cl. ..................................................... 623/1.23
(58) Field of Classification Search ................ 623/1.23, 623/1.13; 227/175.1; 606/153; 128/898; 604/540–541, 544
See application file for complete search history.

(56) References Cited

U.S. PATENT DOCUMENTS

| | | | | |
|---|---|---|---|---|
| 2,453,056 A | * | 11/1948 | Zack ........................... | 606/153 |
| 4,592,354 A | * | 6/1986 | Rothfuss .................... | 227/179.1 |
| 4,705,039 A | * | 11/1987 | Sakaguchi et al. .......... | 606/154 |
| 5,104,025 A | * | 4/1992 | Main et al. ................. | 227/175.1 |
| 5,141,516 A | * | 8/1992 | Detweiler ................... | 606/154 |
| 5,222,963 A | * | 6/1993 | Brinkerhoff et al. ........ | 606/153 |
| 5,250,058 A | * | 10/1993 | Miller et al. ................ | 606/154 |

(Continued)

FOREIGN PATENT DOCUMENTS

DE    38 20 466    2/1990

(Continued)

OTHER PUBLICATIONS

Thiede, "Rectal stapler. A simple instrument for alleviating reconstruction of the colorectal passage in the pelvis," *Chirurg.*, 63:72-73 (1992).

(Continued)

*Primary Examiner*—Julian W Woo
*Assistant Examiner*—Son Dang

(57) ABSTRACT

The invention relates to medical devices, in particular condoms/drains, that find use in anastomosis. Thus the present invention relates to these medical devices per se, to a medical kit comprising these medical devices, to the use of these medical devices, to a method for medical treatment involving application of these medical devices to an organism who is in need thereof as well as to the use of certain biocompatible, biodegradable synthetic polymers in the preparation of a medical device for the treatment of a disease or a condition which requires anastomosis.

The medical devices of the present invention are typically condom shaped and are used for the protection of anastomosis. The devices comprise a tubular shaped part which is made of a biocompatible, biodegradable polymer. The devices may be applied by stapling.

12 Claims, 5 Drawing Sheets

U.S. PATENT DOCUMENTS

| | | | |
|---|---|---|---|
| 5,881,943 A * | 3/1999 | Heck et al. | 227/176.1 |
| 6,126,594 A * | 10/2000 | Bayer | 600/184 |
| 6,523,540 B1 * | 2/2003 | Harrison | 128/844 |
| 6,540,758 B1 * | 4/2003 | Raza | 606/153 |
| 6,585,773 B1 * | 7/2003 | Xie | 623/23.7 |
| 7,128,748 B2 * | 10/2006 | Mooradian et al. | 606/151 |
| 7,401,722 B2 * | 7/2008 | Hur | 227/179.1 |
| 2002/0052649 A1 * | 5/2002 | Greenhalgh | 623/1.35 |
| 2002/0087176 A1 * | 7/2002 | Greenhalgh | 606/155 |
| 2003/0050664 A1 * | 3/2003 | Solem | 606/213 |
| 2003/0183671 A1 | 10/2003 | Mooradian et al. | 227/175.1 |
| 2005/0228363 A1 * | 10/2005 | Leiboff | 604/541 |
| 2006/0142736 A1 * | 6/2006 | Hissink et al. | 604/540 |
| 2007/0043434 A1 * | 2/2007 | Meerkin et al. | 623/1.49 |
| 2008/0228175 A1 * | 9/2008 | Snell et al. | 604/544 |
| 2009/0318898 A1 * | 12/2009 | Dein | 604/541 |

FOREIGN PATENT DOCUMENTS

| | | |
|---|---|---|
| NL | 9 302 140 | 7/1995 |
| WO | WO 89/05830 | 6/1989 |
| WO | WO 03/088854 | 10/2003 |
| WO | WO 2004/039424 | 5/2004 |

OTHER PUBLICATIONS

Yoon et al., Intraluminal bypass technique using a condom for protection of colonanal asastomosis, *Dis. Colon Rectum.*, 37:1046-1047 (1994).

English abstract of DE 3820466.

English abstract of NL 9302140.

* cited by examiner

DEVICES AND METHODS FOR ANASTOMOSIS

RELATED APPLICATIONS

This application is a continuation of PCT application no. PCT/NL2005/000290, designating the United States and filed Apr. 20, 2005; which claims the benefit of the filing date of European application no. 04076251.0, filed Apr. 20, 2004; both of which are hereby incorporated herein by reference in their entirety.

FIELD OF THE INVENTION

The invention relates to medical devices, in particular condoms and drains, that find use in anastomosis. The condoms/drains of the present invention are for example made of biodegradable polyurethanes, in particular polyurethanes comprising poly(ether)ester pre-polymer soft segments and polyurethane hard segments. Thus the present invention relates to these medical devices per se, to a medical kit comprising these medical devices, to the use of these medical devices, to a method for medical treatment involving application of these medical devices to an organism who is in need thereof as well as to the use of certain biocompatible, biodegradable synthetic polymers in the preparation of a medical device for the treatment of a disease or a condition which requires anastomosis.

BACKGROUND OF THE INVENTION

Anastomosis, the operation of joining two ends of biological vessels, such as the oesophagus, colon or other parts of the gastro-digestive channel, is often accompanied by complications. For instance, the most important complication and cause of death following low anterior resection involving the colorectal segment is anastomotic leakage. In many cases re-interventions are needed to treat the complications. Leakage may occur as the result of dehiscence of the anastomosis itself or of the tissue of the digestive channel just proximal or particularly distal of the anastomosis. This may occur typically approximately at around five days after the creation of the anastomosis. Furthermore, there is an increasing use of preoperative radiotherapy of rectal cancer and of the digestive channel in general causing additional problems in anastomotic healing and making the tissue proximal and particularly distal more vulnerable. Quite often a temporary diverting stoma is created to reduce or prevent the complications resulting from an anastomotic leakage. A stoma does not prevent leakage but it drains the gastro intestinal contents before it can get near the newly formed anastomosis. The creation, use and removal of a stoma, restoring the "normal" situation is a burden for the patient and a very costly procedure. To avoid severe complications like peritonitis and septic shock it is important to prevent anastomotic leaks and to take all measures that might eventually be responsible for that complication.

In the art, condoms have been used for the protection of coloanal anastomosis, see e.g. Yoon et al. ("Intraluminal bypass technique using a condom for protection of coloanal anastomosis"; *Dis. Colon Rectum.* 37(1994) 1046-1047). According to this known technique, a sterilized (latex rubber) condom is used to protect a hand sewn coloanal anastomosis. Although this technique is said to be safe, there are still instances of colonic necrosis reported.

SUMMARY

It is an object of the present invention to provide an improvement over prior art materials and techniques for protection of anastomoses.

It was found that this object can be met by providing a device having a tubular shaped part, such as a condom or drain, of a biocompatible, biodegradable synthetic polymer.

DETAILED DESCRIPTION OF THE INVENTION

Figure 1:
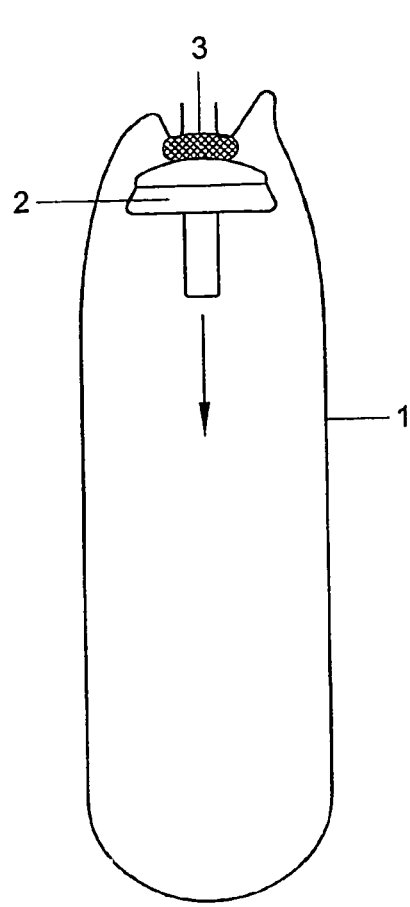
FIG. 1 schematically shows a cross-section of a condom of the present invention prior to application to the site of anastomosis.

In a first aspect, the present invention is directed to a medical device for the protection of an anastomosis, which device comprises a tubular shaped part which is made of a biocompatible, biodegradable polymer. The term "biodegradable" as used herein, means that the material decomposes or looses structural integrity under the conditions it is applied (i.e., in the body). It may thus fragment and leave the body via the natural pathway.

The device of the present invention is preferably in the shape of a condom, viz. having one open end and one closed end. Optionally, a small opening or perforation may be provided in the closed end of the condom of the present invention so as to facilitate the introduction of a stapling cap, as will explained in more detail hereinbelow.

It is a very important property of the devices of the present invention that composition of the biodegradable polymer can be chosen such that a desired and controllable fragmentation behavior, in particular degradation rate, can be obtained. Suitable materials for the condoms or otherwise shaped devices of the present invention are described in WO-A-2004/039424. Particularly suitable polymer compositions are biodegradable polyurethanes. The preferred polyurethane is composed of a poly(ether)ester pre-polymer soft segment and a polyurethane hard segment with a structure -BDI-BDO-BDI-BDO-BDI- (BDI being 1,4-butanediisocyanate and BDO being 1,4-butanediol). The preferred polyether is a polyethyleneglycol. The rate of degradation of the polyurethane will depend on the initial molecular weight (measured by the intrinsic viscosity) and the chemical composition of the pre-polymer. The pre-polymer for this application is preferably based on DL-lactide and ε-caprolactone and has a molecular weight of preferably 1500-2300, more preferably 2000. It may be obtained by a ring opening polymerisation initiated by 1,4-butanediol combined with the polyether compound. The preferred monomer ratio is from 50/50 to 70/30 (mol/mol). The PEG content in the polyurethane is preferably between 1-25 wt. % for applications in the digestive tract, more preferably from 5 to 20 wt. %. In particular, for coloanal anastomosis the PEG content is preferably between 2-10 wt. %. The molecular weight of PEG is preferably between 600-2000 and is most preferably 1000.

Preferably the device of the present invention is manufactured by a spray-coating process comprising the steps of providing a solution of a biocompatible, biodegradable polymer, preferably of the above-mentioned type in a suitable solvent. Suitable solvents are organic solvents, in particular halogenated (in particular chlorated) or non-halogenated lower (typically $C_1$-$C_4$) hydrocarbons (in particular ethers), such as chloroform, dichloromethane, tetrahydrofuran, dioxane and the like. The concentration of the solution is typically from 1 to 10 wt. %, preferably from 2 to 7 wt. %, e.g. about 4 wt. %. The solution is then spraycoated using a known device to a rotating mandrel, which is made from a hard material, e.g. a ceramic material such as glass. The mandrel may have a roughened surface. Subsequently, the solvent is allowed to evaporate. The wall thickness of the device will depend on the amount of polymer solution sprayed on the mandrel. The mandrel and the polymeric layer are submerged in a suitable liquid, such as (distilled) water. Next, the devices of the present invention can be obtained by removing them from the mandrel and cutting them to the desired shape and size and after drying for some time, typically several hours, up to 24 hours, preferably under vacuum at slightly elevated temperatures, such as 25 to 50° C., preferably at about 40° C.

The device of the present invention is suitably manufactured by the following typical spraycoating process wherein the polyurethane as described above is dissolved in a suitable solvent, e.g. chloroform (or dichloromethane, tetrahydrofuran, dioxane, and the like or combinations thereof), ca. 4 wt. %. The polymer solution is spray coated on a horizontally placed and rotating glass mandrel (surface is roughened). After spray coating, the solvent is allowed to evaporate, e.g. during 30 minutes while rotating. The mandrel with the polyurethane layer will be placed in distilled water. The devices will be removed from the mandrel and will be cut to the appropriate shape. The device will be dried e.g. during 24 h under vacuum at 40° C. in order to remove the organic solvent.

The device of the present invention, in particular a condom, preferably has one or more of the following dimensions: a length of 15 to 35 cm (more preferably 25±2 cm); a diameter of 15 to 50 mm (more preferably 35±5 mm); and a wall thickness of 50 to 90 μm (more preferably 70±15 μm).

Figure 8:
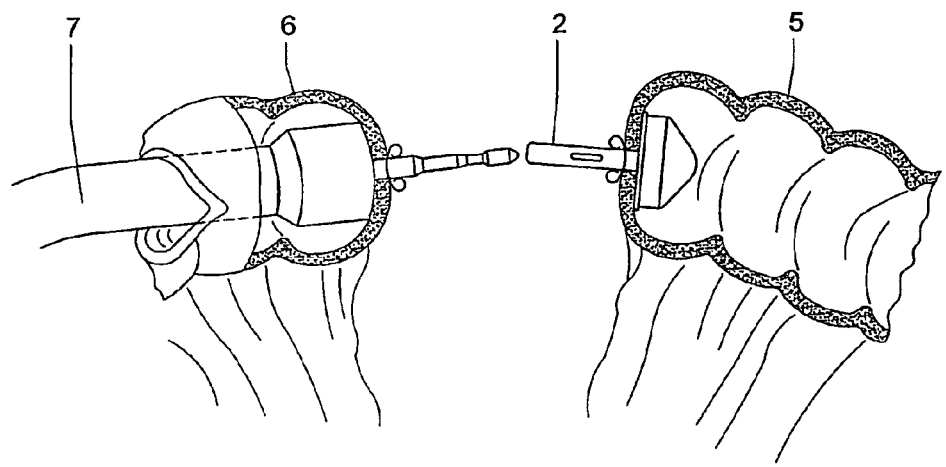
FIG. 8 schematically shows the use of a circular stapler as it is known in the art.

The biodegradable devices of the present invention may be used to perform anastomosis. To this end, it is highly preferred that it is used in combination with a stapler, in particular with a so-called circular stapler. Staplers have been widely accepted for use in colorectal surgery since their introduction in 1975 as an alternative to hand made sutures and are responsible for the increase in the number of procedures in ultra low anterior rectum resection (see Thiede A.; "Rectal stapler. A simple instrument for alleviating reconstruction of the colorectal passage in the pelvis"; *Chirurg.* 63(1992) 72-3). The devices of the present invention can be used in combination with these circular staplers. In FIG. 8, the use of these known circular stapler devices is illustrated: after the cap and stapler are assembled, and the two sections of intestine are aligned, the stapler is closed and fired. Before proceeding to remove the circular stapler, the adjusting knob should be slightly opened to facilitate the extraction of the stapler.

The staples that are suitable for use in the present invention may be made of metal, such as stainless steel, titanium, titanium alloys or cobalt-base alloys, as known in the art. It may also be possible to provide these staples from biodegradable materials, such as biodegradable polymers having the suitable mechanical properties, in particular a suitable ductility.

In principle, any glue may be used to glue the condom to cap (2), since the glue does not contact the body. Preferably, the glue is a cyanoacrylate based glue, which is a typical instant glue for skin applications, e.g. Dermabond™, (JNJ, USA) or Indermil™ (Tyco, USA).

The device of the present invention may thus be used as a drain for different purposes, such as a colorectal drain. The device of the present invention typically supports the newly formed anastomosis for 10 to 15 days by preventing contact between the anastomosis and the contents of the lumen (e.g. the colorectal contents) so that the fresh wound can heal, thereby reducing the chance of complications related to leakage. In accordance with the present invention, the device may be stapled together with the distal and proximal section of the lumen e.g. the intestine, using the known stapling processes e.g. involving the use of a circular stapler device. The temporary drain thus provided, supports the newly formed anastomosis for a sufficient period of time e.g. from 10 to 15 days, after which it will fragment and leave the body via the natural pathway. The device may be synthetic, making it 100% biologically safe.

Figure 10:
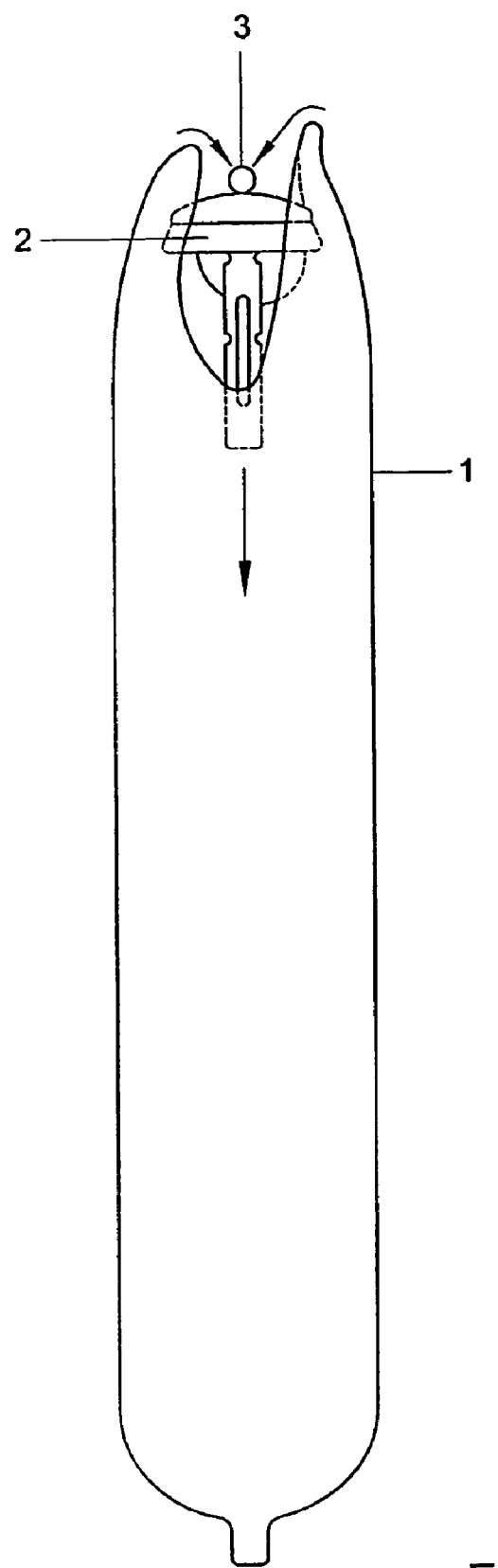
FIG. 10 is an impression of a condom according to the present invention.

The application of the device of the present invention will now be described in more detail with particular reference to the figures, which show the application of a condom according to the present invention. In FIG. 1, the open end (top in FIG. 1) of a drain or condom of the invention (1) is fixed to a stapler cap (2), e.g. using glue (3) that is applied to the top of the cap (2). Note that FIG. 1 is a cross-section and therefore the flaps, as depicted in FIG. 10, are not visible. Preferably, the condom has flaps, which are attached to cap (2), as discussed in more detail hereinbelow. Fixation can be achieved e.g. by using a cyanoacrylate glue. Because the glue does not come in contact with the body, these skin-glues, as well as other types of glue, can be used safely as long as the glue connection is strong enough to pull out the condom (see also FIGS. 5 and 6). The cap and device according to the present invention are preferably dry before the application of glue for optimal adhesion.

The cap (2) is moved in the direction indicated by the arrow in FIG. 1. The pin shaped bottom end of the cap is pierced through the closed end (bottom in FIG. 1) of the condom. A hole or a perforation may be present in the condom to facilitate puncturing of the condom.

Figure 2:
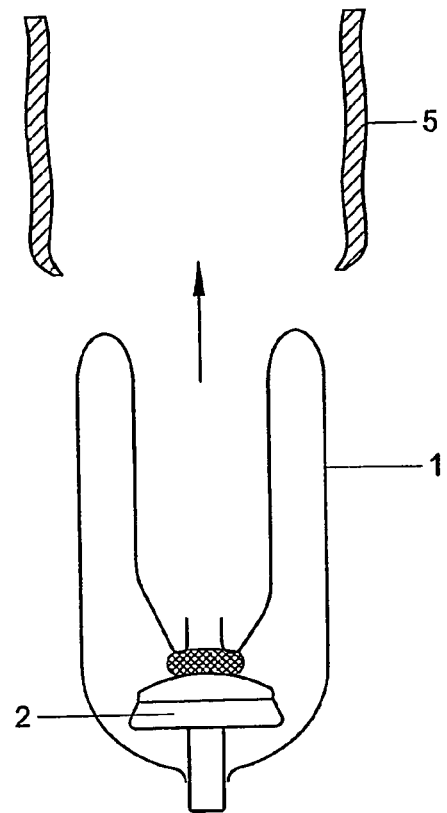
FIG. 2 schematically shows a cross-section condom of the present invention at the time it is applied to the site where the anastomosis is to be performed.
Figure 2:
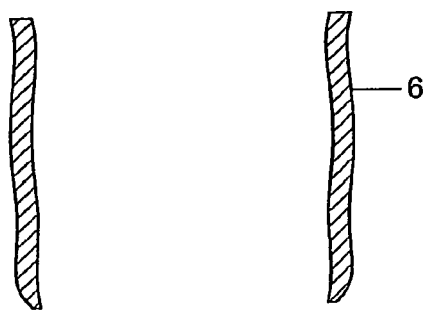

The assembly (condom (1) glued to cap (2)) is then inserted in the proximal section of the intestine (5), see FIG. 2. It is ensured that the drain is placed upward and not folded at the site of the pin.

Figure 3:
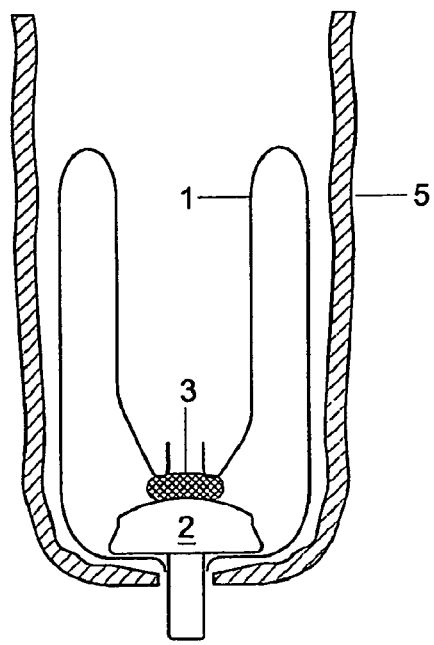
FIG. 3 schematically shows a cross-section of a condom of the present invention at the time it is brought into place in the proximal part of a lumen, prior to stapling.
Figure 9:
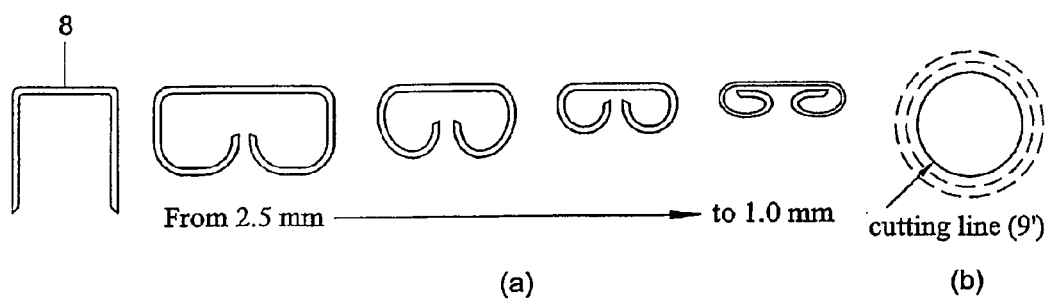
FIG. 9 schematically shows a staple for use known in the art and also with the present invention. It also shows a pattern in which the staples may be applied.

Next, the proximal intestine (5) is closed around the connecting pin (2), see FIG. 3 by means of a so called purse string, known to the skilled person. A stapler device, in particular a circular stapler (7) is inserted in the distal end of the intestine (6). The stapler (7) also has a connecting pin, which fits on the connecting pin of the cap (2), e.g. by the stapler (7) having a female pin and the cap (2) having a male pin, so that both cap (2) and stapler (7) can be connected. The stapler (7) is further provided with staples (8) and an annular knife (9) to cut the intestine and the condom; see also FIGS. 8 and 9.

Figure 4:
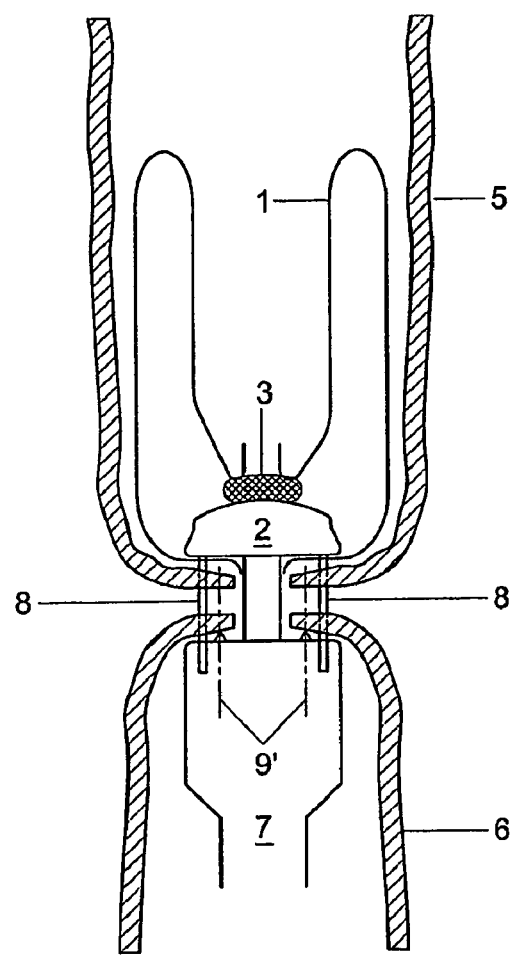
FIG. 4 schematically shows a cross-section of a condom of the present invention just after the stapling has been carried out but prior to the cutting of an annulus.

In FIG. 4, the pin (2) is connected to the stapler device (7). Subsequently both ends of the intestine and the condom (2) are connected in one single staple action. Also a circular portion of the intestine and the condom is cut out leaving an opening as indicated by the dashed line (9'). When the two ends of the intestine are connected by stapling using a circular stapler, the drain according to the present invention is firmly attached at the proximal end of the intestinal wall by the staples.

Figure 5:
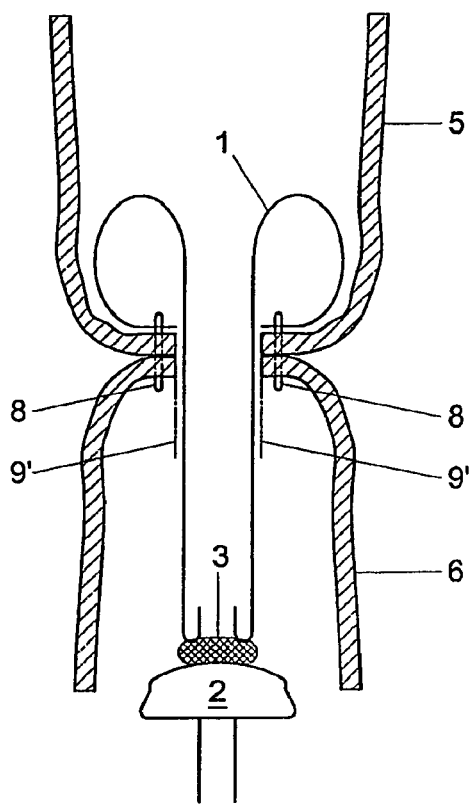
FIG. 5 schematically shows a cross-section of a condom of the present invention at the time the stapling is carried out and the cap is removed from the stapling site.

After the stapling procedure the cap with the condom still fixed to it is pulled through the opening indicated by (9') in a direction further proximal to the anastomosis, as illustrated in FIG. 5. The drain is thereby pulled inside out.

Figure 6:
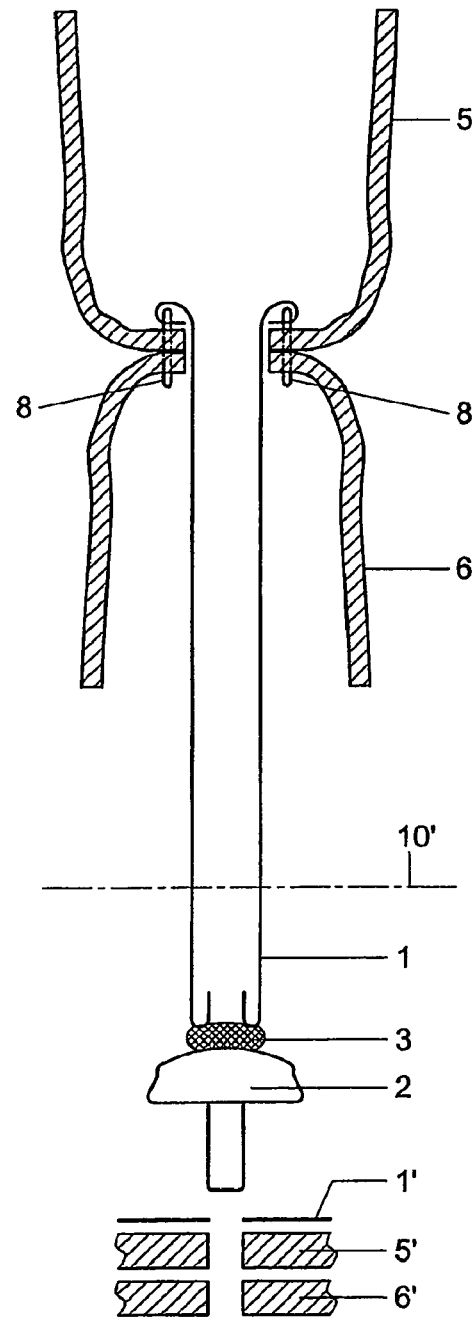
FIG. 6 schematically shows a cross-section of a condom of the present invention at the time it is stretched to its final length and position.

FIG. 6 illustrates the situation wherein the condom is in its proper position to protect the anastomosis. The condom (1) is cut to remove the cap (2). It may be cut at a suitable position, indicated by dashed line (10'). This may be at a position before or after the anal sphincter. Depending on the position of the anastomosis, and upon the discretion of the operator, the loose end may be drawn through the anal sphincter. In case it is too long, or the operator may want to leave it in place on the inside only, it can be cut to the appropriate length. To avoid obstruction of the drain, e.g. due to torsion, the patency of the drain should be checked directly after placement.

Figure 7:
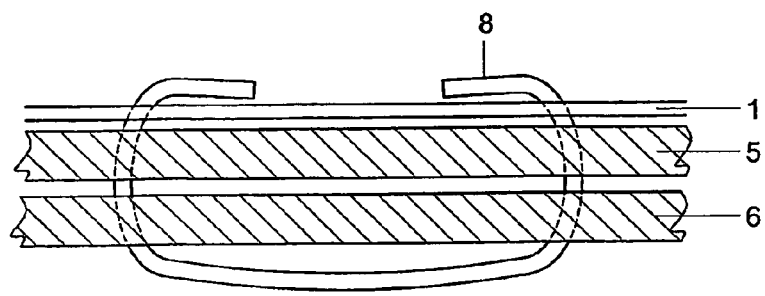
FIG. 7 is a schematic cross-sectional representation, illustrating the position of the staple relative to the device of the present invention and the two ends of the connected lumen.

In FIG. 7, the position of a staple is illustrated, showing that the two ends of the intestine (5) and (6) are connected together with the condom (1) by staple (8). At two weeks, or when the patient is released from the hospital, the part of the drain, which is extra-corporal should be removed.

Then the remaining part of the drain will stay in the lumen of the rectum until it degrades and is removed from the body via the natural pathway.

A medical kit according to the comprises a device as defined above and typically instructions for use. It may further comprise one or more staples, preferably biodegradable staples. It may further comprise a stapling cap, a stapler and/or glue (e.g. a cyanoacrylate glue as mentioned hereinabove). It is also possible to provide the glue already on the cap, and/or on the (flaps of the) condom, while sealing this glue from the environment e.g. by a covering sheet which can be removed upon use so that the glue remains sticky.

The known staplers typically apply a double-staggered circular line of staples, as is illustrated in FIG. 9b showing a typical double-staggered pattern. FIG. 9a shows how the staple height may vary in the course of application. The cutting line is cut out (transected) by knives (9) upon which the tissue within the circle is removed.

The condoms of the present invention may have one or more flaps on the open end to facilitate gluing to the cap. FIG. 10 shows such a preferred embodiment, wherein the condom is provided with two flaps on the top end. These flaps may have a length that is typically about the same size as the diameter of the condom, e.g. 30 mm. Typically, the condom is shaped at the open end as a sinusoid, making two full periods around the circumference of the condom, as illustrated in FIG. 10.

The invention claimed is:

1. A method of treating a human or animal organism comprising
    inserting a tube formed from a biocompatible, biodegradable polymer into a lumen at a point of a desired anastomosis,
    joining two ends of biological vessels together to create an anastomosis, and with one end of the tube being firmly attached to a proximal end of the anastomosis,
    inverting the tube by drawing the other end of the tube through the anastomosis and extending through the anastomosis such that the tube allows natural contents of the lumen to drain through and with the tube shielding the anastomosis in the organism from the natural contents of the lumen.

2. The method of claim 1, wherein the tube is stapled to the lumen forming the anastomosis.

3. The method of claim 1, further comprising biodegradation of the tube.

4. The method of claim 1, wherein the anastomosis is coloanal anastomosis and wherein tube is applied by accessing the intestine essentially via the anal sphincter.

5. The method of claim 1, wherein the polymer is an elastic, biocompatible, biodegradable synthetic polymer, which polymer has at least one softening point of at most mammalian body temperature.

6. The method of claim 1, wherein the polymer comprises a polyurethane, having a molecular weight of between 1500-2300 and which is obtainable by a ring opening polymerization initiated by 1,4-butanediol combined with a polyether compound wherein the monomer ratio is from 50/50 to 70/30 (mol/mol), the PEG content in the polyurethane is between 1-25 wt. % and the molecular weight of PEG is between 600-2000.

7. The method of claim 6, wherein the polyurethane comprises DL-lactide and s-caprolactone.

8. The method of claim 6, wherein the PEG content in the polyurethane is between 5 to 20 wt. %.

9. The method of claim 6, wherein the PEG content in the polyurethane is between 2-10 wt. %.

10. The method of claim 6, wherein the molecular weight of PEG is 1000.

11. The method of claim 1 wherein the tube is a tubular condom.

12. The method of claim 1 wherein the tube supports the anastomosis for 10 to 15 days before fragmenting.

* * * * *